(12) United States Patent
Ruser et al.

(10) Patent No.: US 8,236,537 B2
(45) Date of Patent: *Aug. 7, 2012

(54) FERULATE ESTERASE PRODUCING STRAINS FOR THE ENHANCEMENT OF BIOGAS PRODUCTION

(75) Inventors: Barbara G. Ruser, Buxtehude (DE); William Rutherford, Des Moines, IA (US); Brenda Smiley, Granger, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 478 days.

This patent is subject to a terminal disclaimer.

(21) Appl. No.: 12/357,487

(22) Filed: Jan. 22, 2009

(65) Prior Publication Data

US 2009/0162913 A1    Jun. 25, 2009

Related U.S. Application Data

(63) Continuation-in-part of application No. 11/217,764, filed on Sep. 1, 2005, now Pat. No. 7,799,551.

(60) Provisional application No. 60/606,389, filed on Sep. 1, 2004.

(51) Int. Cl.
  *C12P 5/02* (2006.01)
  *C12N 9/00* (2006.01)
  *C12N 1/20* (2006.01)

(52) U.S. Cl. ............ 435/167; 435/183; 435/252.9

(58) Field of Classification Search .......... None
  See application file for complete search history.

(56) References Cited

U.S. PATENT DOCUMENTS

| | | | |
|---|---|---|---|
| 4,820,531 A | 4/1989 | Tomes | |
| 4,842,871 A | 6/1989 | Hill | |
| 4,863,747 A | 9/1989 | Tomes | |
| 4,981,705 A | 1/1991 | Tomes | |
| 5,026,647 A | 6/1991 | Tomes et al. | |
| 5,292,657 A | 3/1994 | Rutherford et al. | |
| 5,725,853 A | 3/1998 | Dennis et al. | |
| 5,747,020 A | 5/1998 | Rutherford et al. | |
| 6,054,148 A | 4/2000 | Rust et al. | |
| 6,143,543 A * | 11/2000 | Michelsen et al. | 435/196 |
| 6,326,037 B1 | 12/2001 | Mann et al. | |
| 6,337,068 B1 | 1/2002 | Hendrick et al. | |
| 6,403,084 B1 | 6/2002 | Chan et al. | |
| 6,489,158 B1 | 12/2002 | Hendrick et al. | |
| 6,602,700 B1 | 8/2003 | Li et al. | |
| 6,699,514 B2 | 3/2004 | Mann | |
| 6,750,051 B2 | 6/2004 | Tricarico et al. | |
| 7,132,589 B2 | 11/2006 | Dunn-Coleman et al. | |
| 7,453,023 B2 | 11/2008 | Dunn-Coleman et al. | |
| 7,799,551 B2 | 9/2010 | Nsereko et al. | |
| 7,919,683 B2 | 4/2011 | Smiley et al. | |
| 2003/0024009 A1 | 1/2003 | Dunn-Coleman et al. | |
| 2004/0247568 A1 | 12/2004 | Guerino et al. | |
| 2006/0005270 A1 | 1/2006 | Dunn-Coleman et al. | |
| 2006/0046292 A1 | 3/2006 | Nsereko et al. | |
| 2008/0138461 A1 | 6/2008 | Chan et al. | |
| 2008/0138462 A1 | 6/2008 | Chan et al. | |
| 2008/0138463 A1 | 6/2008 | Chan et al. | |
| 2009/0010903 A1 | 1/2009 | Nsereko et al. | |
| 2009/0011085 A1 | 1/2009 | Nsereko et al. | |
| 2009/0028991 A1 | 1/2009 | Chan et al. | |
| 2009/0028992 A1 | 1/2009 | Chan et al. | |
| 2009/0028993 A1 | 1/2009 | Chan et al. | |
| 2011/0154533 A1 | 6/2011 | Smiley et al. | |

FOREIGN PATENT DOCUMENTS

| | | |
|---|---|---|
| EP | 0 880 323 | 6/2001 |
| WO | WO 92/10945 | 7/1992 |
| WO | WO 93/13786 | 7/1993 |
| WO | WO 96/17525 | 6/1996 |
| WO | WO 00/00040 A1 | 1/2000 |
| WO | WO 02/39825 A2 | 5/2002 |
| WO | WO 02/068666 | 9/2002 |
| WO | WO 03/043411 | 5/2003 |
| WO | WO 2006/007395 A1 | 1/2006 |
| WO | WO 2006/026763 A1 | 3/2006 |

OTHER PUBLICATIONS

Jarvis et al. Biomass and Bioenergy (1997), 12(6), 453-460.*
Driehuis et al. Grass and Forage Science, vol. 56, p. 330-343, 2001.*
Donaghy et al. Appl Microbiol Biotechnol. Aug. 1998;50(2):257-60.*
Crepin, et al., "A non-modular type B feruloyl esterase from Neurospora crassa exhibits concentration-dependent substrate inhibition", Biochem. J. (2003), 370:417-427.
Donaghy et al, "Detection of ferulic acid esterase production by Bacillus spp. and lactobacilli", Appl. Microbiol. Biotech., (1998),50:257-260.
Erasmus et al., "Effect of Yeast Culture Supplement on Production, Rumen Fementation, and Duodenal Nitrogen Flow in Dairy Cows", J. Dairy Sci., (1992), 75:3056-3065.
Faulds et al., "Purification and characterization of a ferulic acid esterase (FAE-III) from *Aspergillus niger*, specificity for the phenolic moiety and binding to microcrystalline cellulose", Microbiology, (1994), 140:779-787.
Oba et al., "Effects of Brown Midrib 3 Mutation in Corn Silage on Dry Matter Intake and Productivity of High Yielding Dairy Cows", J. Dairy Sci. (1999), 82:135-142.
Wohlt et al., "Effect of Yeast on Feed Intake and Performance of Cows Fed Diets Based on Corn Silage During Early Lactation", J. Dairy Sci., (1998), 81:1345-1352.
Collins, Matthew D., et al., "Deoxyribonucleic Acid Homology Studies of *Lactobacillus casei, Lactobacillus paracasei* sp. nov., subsp. *paracasei* and subsp.*tolerans*, and *Lactobacillus rhammosus* sp. nov., comb. nov.," *International Journal of Systematic Bacteriology*, 1989, vol. 39(2), pp. 105-108.
Loc, Nguyen Thi, et al., "Cassava Root Silage for Crossbred Pigs Under Village Conditions in Central Vietnam," *Livestock Research for Rural Development*, 1997, vol. 9(2), http://www.fao.org/ag/aga/agap/frg/feedback/lrrd/lrrd9/2/loc922.htm (12 pages, printed from Internet Nov. 17, 2009).

(Continued)

*Primary Examiner* — Christian Fronda
(74) *Attorney, Agent, or Firm* — Alston & Bird LLP

(57) ABSTRACT

Compositions of ferulate esterase producing bacterial strains or functional mutants thereof and methods of using ferulate esterase producing bacterial strains as silage inoculants for the enhancement of biogas production are disclosed. Ferulate esterase producing bacterial strains of *Lactobacillus*, including *Lactobacillus buchneri*, or functional mutants thereof are used as silage inoculants to improve the degradation of plant biomass for enhanced production of biogas.

8 Claims, 2 Drawing Sheets

OTHER PUBLICATIONS

Moore, H.I., et al., "Silos and Silage," http://www.smallstock.info/reference/moore/silage.htm (85 pages printed from Internet Nov. 17, 2009).

Tabka, M.G., et al., "Enzymatic saccharification of wheat straw for bioethanol production by a combined cellulase xylanase and feruloyl esterase treatment," *Enzyme and Microbial Technology*, 2006, vol. 39, pp. 897-902.

Wang, Xiaokun, et al., "Purification and Characterization of a Feruloyl Esterase from the Intestinal Bacterium *Lactobacillus acidophilus*," *Applied and Environmental Microbiology*, 2004, vol. 70(4), pp. 2367-2372.

Whiter A.G., et al., "The Effect of a Dry or Liquid Application of *Lactobacillus plantarum* MTD1 on the Fermentation of Alfalfa Silage," *J Dairy Sci.*, 2001, vol. 84, pp. 2195-2202.

International Search Report for PCT/US2005/031489, date of mailing Dec. 28, 2005.

Andesogan, A.T., "Improving Forage Quality and Animal Performance with Fibrolytic Enzymes," *Florida Ruminant Nutrition Symposium*, 2005, pp. 91-109.

Filya, I., "The Effect of *Lactobacillus buchneri* and *Lactobacillus plantarum* on the Fermentation, Aerobic Stability, and Ruminal Degradability of Low Dry Matter Corn and Sorghum Silages," *J Dairy Sci.*, 2003, vol. 86, pp. 3575-3581.

Hill, J., et al., "Effect of inoculation of herbage prior to ensiling with *Streptomyces achromogenes* ISP 5028 on chemical composition of silage," *Animal Feed Science and Technology*, 2001, vol. 89, p. 83-96.

Holzer, M., et al., "The Role of *Lactobacillus buchneri* in Forage Preservation," *Trends in Biotechnology*, 2003, vol. 21(6), pp. 282-287.

Kleinschmit, D.H., and L. Kung, "A Meta-Analysis of the Effects of *Lactobacillus buchneri* on the Fermentation and Aerobic Stability of Corn and Grass and Small-Grain Silages," *J. Dairy Sci.*, 2006, vol. 89(10), pp. 4005-4013.

Nsereko, V., et al., "Influence of inoculating forage with lactic acid bacterial strains that produce ferulate esterase on ensilageand ruminal degradation of fiber," *Animal Feed Science and Technology*, 2008, vol. 145, pp. 122-135.

Ranjit, N. K., and L. Kung, "The Effect of *Lactobacillus buchneri*, *Lactobacillus plantarum*, or a Chemical Preservative on the Fermentation and Aerobic Stability of Corn Silage," *J. Dairy Sci.*, 2000, vol. 83, pp. 526-535.

Schrag, J.D., and M. Cygler, "Lipases and $\alpha/\beta$ Hydrolase Fold," *Methods in Enzymology*, 1997, vol. 284, pp. 85-107.

Taylor, C.C., et al., "*Lactobacillus buchneri* and Enzymes Improves the Aerobic Stability of High Moisture Corn," *J. Anim. Sci.*, 2000, vol. 78(Supp 1) p. 111, (Abstract 477).

* cited by examiner

FERULATE ESTERASE PRODUCING STRAINS FOR THE ENHANCEMENT OF BIOGAS PRODUCTION

CROSS REFERENCE TO RELATED APPLICATIONS

This application is a Continuation-in-Part to U.S. patent application Ser. No. 11/217,764, filed on Sep. 1, 2005 which claims the benefit of and priority of U.S. Provisional Application No. 60/606,389, filed on Sep. 1, 2004, which are herein incorporated by reference in their entirety.

FIELD OF THE INVENTION

The claimed invention relates to organisms that produce ferulate esterase and methods of using the same for the enhancement of biogas production. In particular, the claimed invention relates to ferulate esterase producing bacterial strains of *Lactobacillus* or functional mutants thereof. Lactic acid bacteria capable of producing the enzyme ferulate esterase are used as silage inoculants which enhances the degradation of plant biomass for the enhanced production of biogas.

BACKGROUND OF INVENTION

Biogas is a mixture of primarily methane and carbon dioxide gases. It is considered to be a low-grade natural gas, as it contains approximately from 50-65% methane. In comparison, natural gas contains approximately from 90-95% methane. Biogas is seen as a cost-efficient or low-cost fuel, as it is a renewable fuel.

Biogas is produced when bacteria convert organic matter to methane. Organic matter is the food source for methane-producing bacteria. For farm-based biogas production, the primary organic matter source is manure. Although biogas can be produced using manure as the only organic source, research has shown that gas production can be greatly increased by adding additional substrates. For example, the most common substrate is derived from energy crops such as corn silage. However, the digestion of fiber has been shown to be a limiting factor in the use of such energy crops, such as silage.

The plant cell wall is a complex structure consisting of different polysaccharides, the major components being cellulose, hemicelluloses and pectins. These polysaccharides may be cross-linked, or linked to lignin by phenolic acid groups such as ferulic acid. Ferulic acid may play a role in the control of cell wall growth in the plant and ferulic acid cross-linking within the cell wall is believed to restrict cell wall digestion by microorganisms (Fry et al., (1983) Planta 157: 111-123; and Borneman et al., (1990) Appl. Microbial. Biotechnol. 33: 345-351). Some microorganisms are known to exhibit ferulic acid esterase activity (ferulate esterase) and thereby facilitate the breakdown of plant cell walls and fiber digestion (U.S. Pat. No. 6,143,543). U.S. patent application Ser. No. 11/217,764 demonstrates the importance of methods and compositions to decrease the resistance of the plant cell wall to digestion for improvements in the animal production industry through the use of silage inoculants, forage additives and other amendments that improve the digestibility of feed.

The feed industry has used various treatments for ensiled feed or other animal feed with fiber degrading enzymes, including, for example: fungi, including various mold sources, to improve feed digestibility; *Saccharomyces cerevisiae* yeast strains fed directly to cattle to improve fiber digestion (Erasmus et al., (1992) J. Dairy Sci. 75: 3056-3065; and Wohlt et al., (1998) J. Dairy Sci. 81: 1345-1352); direct microbial feeds, including a species of *Lactobacillus* (WO-A-93/3786; and U.S. Pat. No. 6,699,514); feeding a diet inherently possessing good digestibility characteristics, including for example, brown midrib corn silage (Oba and Allen, (1999) J. Dairy Sci. 82: 135-142), or alternatively, highly digestible corn hybrids; and technologies incorporating fungal gene(s) for the production of ferulate esterase into plant tissue for subsequent expression, resulting in improvements in fiber digestibility (WO 02/68666).

The successful enhancement of fiber digestion in the rumen of an animal results in the animal getting more from its feed. As a result, the animal demonstrates increased milk yield, in dairy cows, and beef production in forage fed animals. Accordingly, farmers either tolerate a lower level of feed digestibility from silage, and therefore productivity, or use inoculants, forage additives or other feed additives to improve digestibility of feed.

There are significant intrinsic similarities between the need for improved digestion of silage in the rumen of an animal and anaerobic biogas digestion. As a result, the biogas industry has extensively considered methods for improving the production of biogas from energy crops such as corn silage.

The utilization of energy crops for stimulation of biogas production yields similar limitations as those observed in feed digestion. Namely, the fiber fraction of crops is difficult to degrade, such that the fiber portion of the biomass is the first and rate-limiting step in the production of biogas from energy crops, including for example, corn.

To overcome the limitation of fiber degradation of organic sources, namely silage such as corn, a cocktail of fiber-degrading enzymes may be applied directly to the anaerobic digester or to the silage prior to delivery to the digester. In this instance, the applied enzymes work to partially degrade the fiber fractions, releasing simple substrates such as sugars and carbohydrates to provide additional energy to the methane-producing bacteria. The result is increased fiber degradability. However, neither the typical fermentor nor silage provides ideal conditions for the actions of these enzymes. Therefore, fiber degradation will continue to proceed at a relatively slow rate.

An additional means to overcome the limitation of fiber degradation in organic silage sources is to increase its surface area. The degradation of particulate fiber material is dependant upon the availability of surface area for exogenous enzyme or bacterial attachment. The smaller the particle size of the matter results in a greater surface area. As a result of such increased surface area, the rate and the extent of digestion of the fiber fraction are both faster and greater. Silage from energy crops has a large particle size due to the necessity for packing such silage to exclude air. Additionally, reduced particle size affects the function of an animal's rumen, such that inadequate effective fiber is available to stimulate the rumen. Accordingly, the optimal conditions for silage management and animal feeding are not the same as those needed for optimal degradation of fiber to produce methane.

Processing silage in order to reduce its particle size can be used to further increase the digestion of the fiber fraction in methane generators. However, the technique requires specialized equipment, additional handling and energy inputs to improve the production of methane. As a result, such processes are not cost-effective for biogas production.

Accordingly, it is an objective of the claimed invention to provide methods for enhancing the production of biogas through the use of silage inoculants to improve the degradation of the fiber portion of the organic materials.

A further object of the invention is a method for treating pre-ensiled plant material to enhance the production of biogas.

A further object of the invention is a method for enhancing biogas production yielding an increased rate and increased extent of digestion of fiber fractions.

A further object of the invention includes compositions for use as silage inoculants.

SUMMARY OF THE INVENTION

It has now been found that ferulate esterase producing bacterial strains or functional mutants thereof are suitable compositions for use as silage inoculants for enhancing biogas production. Further, it has been found that biogas production, namely methane production, is enhanced by using a biogas enhancing effective amount of a ferulate esterase containing composition, wherein the ferulate esterase is derived from a ferulate esterase producing bacterial strain or functional mutant thereof.

Embodiments of the present invention provide both compositions and methods of using silage inoculants of ferulate esterase producing bacterial strains disclosed herein. The compositions and methods of the claimed invention further pertain to the use of lactic acid bacteria capable of producing the enzyme ferulate esterase and its use as a silage inoculant to enhance plant biomass degradation during anaerobic digestion conditions to produce biogas.

DETAILED DESCRIPTION OF THE INVENTION

Figure 1:
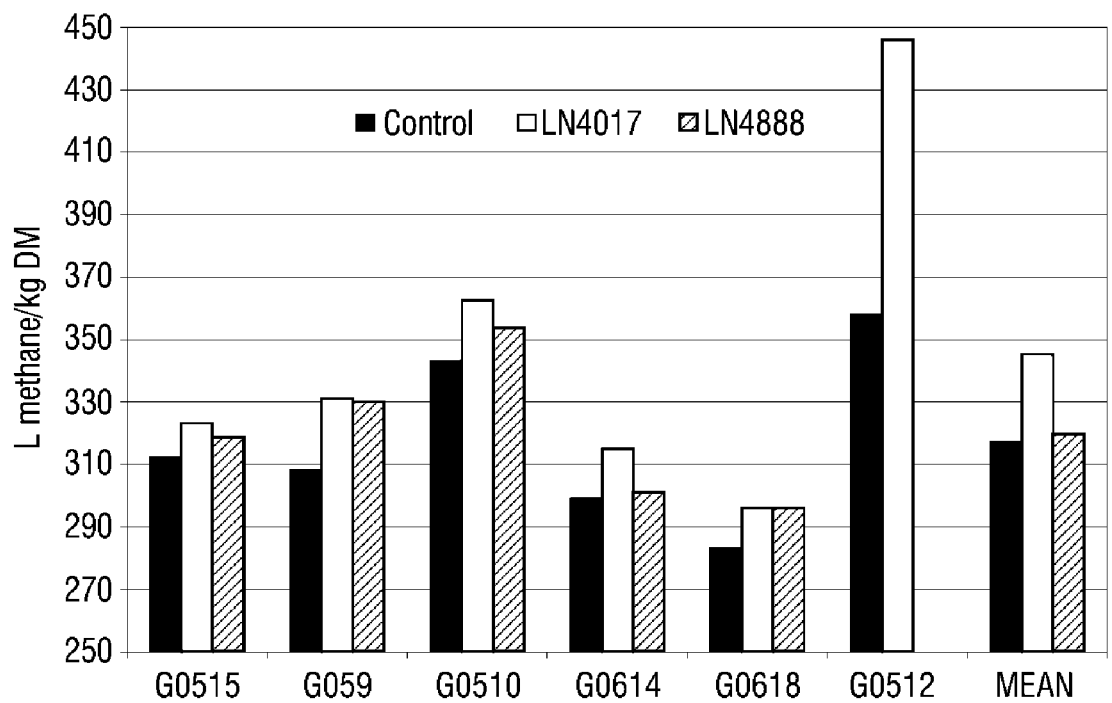
FIG. 1 shows the effect of *Lactobacillus buchneri* treatment on methane production from whole plant corn silage.

The embodiments of this invention are not limited to particular compositions or methods of enhancing biogas production, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Thus, for example, reference to a "component" can include a combination of two or more components; reference to "feed" can include mixtures of feed, and the like.

Further, all units, prefixes, and symbols may be denoted in its SI accepted form. Numeric ranges recited within the specification are inclusive of the numbers defining the range and include each integer within the defined range.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "digestibility," as used herein, refers to the ability to derive soluble nutrients from a feed plant material. Digestibility can be determined, e.g., by analyses that provide assay data indicating the amount of feed residue remaining in a digestion and/or by analyses that provide assay data indicating the amount of nutrients released from feed in a digestion.

The term "functional mutant" means a bacterial strain directly or indirectly obtained by genetic modification of, or using, the referenced strain(s) and retaining at least 50% of the activity of a control silage using the referenced strain. The genetic modification of a functional mutant can be achieved through any means, such as, but not limited to, chemical mutagens, ionizing radiation, transposon-based mutagenesis, or via conjugation, transduction, or transformation using the referenced strains as either the recipient or donor of genetic material.

The term "inoculation," as used herein, refers to introduction of viable microbes to media or feed plant material.

The term "isolated" means removed from a natural source such as from uninoculated silage or other plant material.

The term "plant material," as used herein, refers to material of plant origin. Feed plant material can be plant material intended to be fed to an animal.

The term "pre-ensiled plant material" means grasses, maize, alfalfa and other legumes, wheat, sorghum, sunflower, barley and mixtures thereof, all of which can be treated successfully with the inoculants of the embodiments of the present invention. The inoculants of the embodiments of the present invention are also useful in treating high moisture corn (HMC).

The term "purified" means that a bacterial species or strain is substantially separated from, and enriched relative to: yeasts, molds, and/or other bacterial species or strains found in the source from which it was isolated.

The term "silage" as used herein is intended to include all types of fermented agricultural products, including for exemplary purposes only, grass silage, alfalfa silage, wheat silage, legume silage, sunflower silage, barley silage, whole plant corn silage, sorghum silage, fermented grains and grass mixtures, etc.

An embodiment of the invention is a composition of and methods for the use of lactic acid bacteria which produce the enzyme ferulate esterase. The methods of the invention disclose the use of such ferulate esterase producing bacteria as silage inoculants to enhance the degradation of plant biomass during anaerobic digestion for the production of biogas. The ferulate esterase cleaves ferulic acid ester cross-linkages between lignin and polysaccharides and between polysaccharides themselves.

Various strains of lactic acid bacteria, including for example, *Lactobacillus buchneri* LN4017 and LN4888 (PTA-6738 and NRRL B-30866) produce ferulate esterase, which not only enhance the digestibility of energy crops' fiber content, but also enhances both the rate and extent of biogas generation. The enhancement of fiber digestion in ruminants is directly applicable to the biomass degradation required for biogas production. The rate-limiting step in the anaerobic conversion of plant material to methane is the breakdown of complex fiber polysaccharides. The complex polysaccharides must be broken down into simple sugars in order to be converted to methane.

The long incubation of ferulate esterase producing bacteria in the ensiled forage results in modifications of the lignin-polysaccharide complex making it easier for biomass degrading organisms to convert the indigestible fiber to simple carbohydrates, which are then converted to methane.

In one embodiment of the invention, the ensiling of whole plant corn forage can be treated with a catalytic amount of a ferulate esterase producing bacteria. The fermentation occurring during the ensiling process provides ample time for modifications to the ferulate cross linkages between lignin and polysaccharide or the polysaccharides themselves. As a result, when the corn silage is added to the biogas generator, the production of methane increases both in total amount and in the rate of digestion when compared to an untreated control.

A further embodiment of the invention is a composition for use as a silage inoculant comprising a ferulate esterase producing bacterial strain or a functional mutant thereof and a suitable carrier. Suitable ferulate esterase producing bacterial strains or functional mutants thereof include *Lactobacillus* strains. Suitable ferulate esterase producing *Lactobacillus* strains or functional mutants thereof include *Lactobacillus buchneri, Lactobacillus plantarum, Lactobacillus brevis, Lactobacillus reuteri, Lactobacillus alimentarius, Lactobacillus crispatus*, and *Lactobacillus paralimentarius* or functional mutant thereof each *Lactobacillus* strain. Suitable ferulate esterase producing *Lactobacillus buchneri, Lactobacillus plantarum, Lactobacillus brevis, Lactobacillus reuteri, Lactobacillus alimentarius, Lactobacillus crispatus*, and *Lactobacillus paralimentarius* or functional mutants thereof each *Lactobacillus* strain, which include *Lactobacillus buchneri*, strain LN4017, deposited as Patent Deposit No. PTA-6138, *Lactobacillus plantarum*, strain LP678, deposited as Patent Deposit No. PTA-6134, *Lactobacillus plantarum*, strain LP3710, deposited as Patent Deposit No. PTA-6136, *Lactobacillus plantarum*, strain LP3779, deposited as Patent Deposit No. PTA-6137, *Lactobacillus plantarum*, strain LP7109, deposited as Patent Deposit No. PTA-6139, *Lactobacillus brevis*, strain LB1154, deposited as Patent Deposit NRRL B-30865, *Lactobacillus buchneri*, strain LN4888, deposited as Patent Deposit NRRL B-30866, *Lactobacillus reuteri*, strain LR4933, deposited as Patent Deposit NRRL B-30867, *Lactobacillus crispatus*, strain LI2127, deposited as Patent Deposit NRRL B-30868, *Lactobacillus crispatus*, strain LI2350, deposited as Patent Deposit NRRL B-30869, *Lactobacillus crispatus* strain LI2366, deposited as Patent Deposit NRRL B-30870, *Lactobacillus* species unknown, strain UL3050, deposited as Patent Deposit NRRL B-30871, and mixtures thereof.

In an embodiment of the invention the composition contains from about $10^1$ to about $10^{10}$ viable organisms of the ferulate esterase producing bacterial strain or functional mutant thereof per gram of a pre-ensiled plant material. In a further embodiment of the invention the composition contains from about $10^2$ to about $10^7$ viable organisms of the ferulate esterase producing bacterial strain or functional mutant thereof per gram of a pre-ensiled plant material. In yet a further embodiment the composition contains from about $10^3$ to about $10^6$ viable organisms of the ferulate esterase producing bacterial strain or functional mutant thereof per gram of a pre-ensiled plant material.

Suitable carriers are either liquid or solid and are well known by those skilled in the art. For example, solid carriers may be made up of calcium carbonate, starch, cellulose and combinations thereof.

The detection of bacterial strains producing ferulate esterase enzyme are completed by utilizing microbial cell lysates. The lysates are assayed for ferulate esterase activity. An embodiment of the invention is the use of *Lactobacillus* bacterial strains or functional mutants thereof, capable of producing ferulate esterase. Additional bacterial strains can be utilized, according to skilled artisans, including *Bacillus* strains obtained from agar screening assays (Donaghy et al., (1998) Appl. Microbiol. Biotechnol. 50: 257-260).

A further embodiment of the invention is a biologically pure culture of *Lactobacillus buchneri*, strain LN4017, ATCC Accession No. PTA-6138. A still further embodiment of the invention is a biologically pure culture of *Lactobacillus buchneri*, strain LN4888, ARS Accession No. NRRL B-30866.

Deposits of the following microorganisms has been made with the American Type Culture Collection (ATCC), 10801 University Blvd., Manassas, Va. 20110-2209: *Lactobacillus buchneri* LN4017 (ATCC Accession No. PTA-6138), *Lactobacillus plantarum* LP678 (ATCC Accession No. PTA-6134), *Lactobacillus plantarum* LP3710 (ATCC Accession No. PTA-6136), *Lactobacillus plantarum* LP3779 (ATCC Accession No. PTA-6137), *Lactobacillus plantarum* LP7109 (ATCC Accession No. PTA-6139), and *Lactobacillus paracasei tolerans* LC3200 (ATTC Accession No. PTA-6135). These organisms were deposited on Aug. 3, 2004. The microorganisms deposited with the ATCC were taken from the same deposit maintained at Pioneer Hi-Bred International, Inc. (Des Moines, Iowa). Applicant(s) will meet all the requirements of 37 C.F.R. §§1.801-1.809, including providing an indication of the viability of the sample when the deposit is made. Each deposit will be maintained without restriction in the ATCC Depository, a public depository, for a period of 30 years, or 5 years after the most recent request, or for the enforceable life of the patent, whichever is longer, and will be replaced if it ever becomes nonviable during that period. These deposits will be maintained under the terms of the Budapest Treaty on the International Recognition of the Deposit of Microorganisms for the Purposes of Patent Procedure. These deposits will irrevocably and without restriction or condition be available to the public upon issuance of a patent. However, it should be understood that the availability of a deposit does not constitute a license to practice the subject invention in derogation of patent rights granted by government action.

The strains indicated below were deposited on Aug. 6, 2005 with the Agricultural Research Service (ARS) Culture Collection, housed in the Microbial Genomics and Bioprocessing Research Unit of the National Center for Agricultural Utilization Research (NCAUR), under the Budapest Treaty provisions. The strains were given the indicated accession numbers: *Lactobacillus brevis* LB1154, ARS Accession No. NRRL B-30865; *Lactobacillus buchneri* LN4888, ARS Accession No. NRRL B-30866; *Lactobacillus reuteri* LR4933, ARS Accession No. NRRL B-30867; *Lactobacillus crispatus* LI2127, ARS Accession No. NRRL B-30868; *Lactobacillus crispatus* LI2350, ARS Accession No. NRRL B-30869; *Lactobacillus crispatus* LI2366, ARS Accession No. NRRL B-30870. The address of NCAUR is 1815 N. University Street, Peoria, Ill., 61604. The deposits will irrevocably and without restriction or condition be available to the public upon issuance of a patent. However, it should be understood that the availability of a deposit does not constitute a license to practice the subject invention in derogation of patent rights granted by government action.

The strain indicated below was deposited on Aug. 16, 2005 with the Agricultural Research Service (ARS) Culture Collection, housed in the Microbial Genomics and Bioprocessing Research Unit of the National Center for Agricultural Utilization Research (NCAUR), under the Budapest Treaty provisions. The strain was given the indicated accession number: *Lactobacillus* species unknown UL3050, ARS Accession No. NRRL B-30871. The address of NCAUR is 1815 N. University Street, Peoria, Ill., 61604. The deposit will irrevocably and without restriction or condition be available to the public upon issuance of a patent. However, it should be understood that the availability of a deposit does not constitute a license to practice the subject invention in derogation of patent rights granted by government action.

A method for treating pre-ensiled plant material to enhance the production of biogas by adding to the pre-ensiled plant material a biogas production enhancing amount of a composition containing a ferulate esterase producing bacterial strain or a functional mutant thereof of is also disclosed. Suitable pre-ensiled plant materials include for example, grasses, maize, alfalfa and other legumes, wheat, sorghum, sunflower, barley and mixtures thereof.

An embodiment of the invention is a method for enhancing production of biogas by inoculating silage with an effective amount of a ferulate esterase containing composition, wherein the ferulate esterase is derived from a ferulate esterase producing bacterial strain or a functional mutant thereof. Suitable ferulate esterase producing bacterial strains or functional mutants thereof include *Lactobacillus* strains. Suitable ferulate esterase producing *Lactobacillus* strains or functional mutants thereof include *Lactobacillus buchneri*, *Lactobacillus plantarum*, *Lactobacillus brevis*, *Lactobacillus reuteri*, *Lactobacillus alimentarius*, *Lactobacillus crispatus*, and *Lactobacillus paralimentarius* or functional mutants thereof each *Lactobacillus* strain. Suitable ferulate esterase producing *Lactobacillus buchneri*, *Lactobacillus plantarum*, *Lactobacillus brevis*, *Lactobacillus reuteri*, *Lactobacillus alimentarius*, *Lactobacillus crispatus*, and *Lactobacillus paralimentarius* or a functional mutant thereof each *Lactobacillus* strain, which include *Lactobacillus buchneri*, strain LN4017, deposited as Patent Deposit No. PTA-6138, *Lactobacillus plantarum*, strain LP678, deposited as Patent Deposit No. PTA-6134, *Lactobacillus plantarum*, strain LP3710, deposited as Patent Deposit No. PTA-6136, *Lactobacillus plantarum*, strain LP3779, deposited as Patent Deposit No. PTA-6137, *Lactobacillus plantarum*, strain LP7109, deposited as Patent Deposit No. PTA-6139, *Lactobacillus brevis*, strain LB1154, deposited as Patent Deposit NRRL B-30865, *Lactobacillus buchneri*, strain LN4888, deposited as Patent Deposit NRRL B-30866, *Lactobacillus reuteri*, strain LR4933, deposited as Patent Deposit NRRL B-30867, *Lactobacillus crispatus*, strain LI2127, deposited as Patent Deposit NRRL B-30868, *Lactobacillus crispatus*, strain LI2350, deposited as Patent Deposit NRRL B-30869, *Lactobacillus crispatus* strain LI2366, deposited as Patent Deposit NRRL B-30870, *Lactobacillus* species unknown, strain UL3050, deposited as Patent Deposit NRRL B-30871, and mixtures thereof.

Compositions that are added to a biogas generator with corn silage have been treated with an effective catalytic amount of the ferulate esterase producing bacterial strain or functional mutant thereof as is readily determinable by those skilled in the art.

A further embodiment of the invention is a substantially purified strain of a bacterium selected from the group consisting of *Lactobacillus buchneri*, strain LN4017, deposited as Patent Deposit No. PTA-6138, *Lactobacillus plantarum*, strain LP678, deposited as Patent Deposit No. PTA-6134, *Lactobacillus plantarum*, strain LP3710, deposited as Patent Deposit No. PTA-6136, *Lactobacillus plantarum*, strain LP3779, deposited as Patent Deposit No. PTA-6137, *Lactobacillus plantarum*, strain LP7109, deposited as Patent Deposit No. PTA-6139, *Lactobacillus paracasei tolerans*, strain LC3200 having ATCC Accession No. PTA-6135, *Lactobacillus brevis*, strain LB1154, deposited as Patent Deposit NRRL B-30865, *Lactobacillus buchneri*, strain LN4888, deposited as Patent Deposit NRRL B-30866, *Lactobacillus reuteri*, strain LR4933, deposited as Patent Deposit NRRL B-30867, *Lactobacillus crispatus*, strain LI2127, deposited as Patent Deposit NRRL B-30868, *Lactobacillus crispatus*, strain LI2350, deposited as Patent Deposit NRRL B-30869, *Lactobacillus crispatus*, strain LI2366, deposited as Patent Deposit NRRL B-30870, *Lactobacillus* species unknown, strain UL3050, deposited as Patent Deposit NRRL B-30871, and mixtures thereof.

In further embodiments of the invention, combinations of the *Lactobacillus* strains enhance plant fiber degradation and the fermentation and aerobic stability of the silage. Methods of using mixed cultures for improving either fermentation or aerobic stability of silage are disclosed in U.S. Pat. No. 6,403,084. Such methods and embodiments of the invention promote the preservation of biomass. Preservation is inherent in the process of using corn silage for the production of biogas and is accomplished by a rapid lowering of pH to inhibit plant respiration and thus loss of biomass. Additionally, the use of specific organisms such as *Lactobacillus* strains, including *Lactobacillus buchneri*, produces metabolic by-products preventing the aerobic deterioration of silage mass upon exposure to oxygen. Up to about 25% of the total biomass may be lost during aerobic deterioration, representing a significant loss of dry matter (DM) that could otherwise be converted to methane in the biogas fermentor. The use of *Lactobacillus* strains, including *Lactobacillus buchneri*, prevents aerobic deterioration of the silage mass and preserves silage for conversion to methane.

In an embodiment of the present invention, the treatment of various forms of silage with *Lactobacillus buchneri* strains produces an increased amount of methane. In a preferred embodiment the silage yields up to as much as 7% more methane from each kilogram of silage tested. In a further preferred embodiment, the efficiency of the *Lactobacillus* treatments showed enhanced methane production over the uninoculated control by nearly 15%. Additionally, the increased methane production correlates to an increase in DM recovery.

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

EXAMPLE 1

Whole plant corn forage (approximately 35% dry matter (DM)) was harvested using a precision forage chopper to a theoretical chop length of from about 10-13 mm. A mixed sward of perennial rye grass was cut and allowed to wilt for one and one-half days to a DM content of approximately 35%. The wilted forage was precision chopped to a theoretical chop length of from about 7-15 mm.

The inoculant was applied to supply at a rate of approximately 105 cfu per gram forage. All treatments were applied by syringe and thoroughly mixed into the forage by rolling on clean plastic sheeting. For each treatment, four experimental 10×36 cm PVC silos were filled with sufficient forage to give a density of approximately 150 kg DM/cubic meter. Silos were stored until opening in a climate controlled chamber at 20 degrees Celsius.

Upon opening, sub-samples of forage were taken for DM determination and aqueous extracts were prepared for HPLC analysis of volatile fatty acids. DM losses were calculated and aerobic stability was determined by the methods described by Honig, H., (1985) Das Wirtschaftseigene Futter 21: 25-32. The remaining forage was frozen for use as a substrate for biogas production.

EXAMPLE 2

Estimates of biogas production were obtained from frozen silage according to the procedure described herein. Neutral density polyethylene containers of approximately 20 Liters were filled with 15 Liters of seeding sludge collected from a municipal waste treatment plant. Each container was equipped with a valve in the lid to allow gas collection. To the 15 Liter seeding sludge, 500 grams fresh silage material was added and the container was tightly sealed. Periodic mixing was accomplished with a mechanical mixer or by shaking of the container.

Resulting gas volumes produced were measured with a drum-type gas volume meter or by volumetric measurement prior to or after collection into a gas-tight analysis bag. Gas composition was measured with a Drager X-am 7000 gas analyzer equipped to monitor carbon dioxide, methane and hydrogen sulfide. Composition readings were taken daily and the volume of methane generated was determined from the methane percentage of the collected gas.

EXAMPLE 3

Treatment of Whole Plant Corn Silage

The treatment of whole plant corn forage with strains of Lactobacillus buchneri, including either strain LN4017 and LN4888, produced quality silage after 60 days of fermentation. TABLE 1 compares the effect of Lactobacillus buchneri treatment on quality of whole plant corn silage with an uninoculated control. The high content of lactic acid results in good preservation of forage in all treatments as evidenced by low fermentation DM losses.

Characteristic of Lactobacillus buchneri fermentation is high amounts of acetic acid produced in relation to lactic acid and such high acetic acid concentrations correlate to the inhibition of spoilage organisms in the silage. Improved aerobic stability of the silage treated with either Lactobacillus buchneri strain LN4017 and LN4888 validates such relationship by showing a nearly 24 hour improvement in stability. In addition to the increased length of time prior to heating, the effects of microbial activity are minimized as shown by the nearly 2% decrease in aerobic DM losses. The total dry matter loss during anaerobic and aerobic fermentation was decreased by 2-2.5% with silage treated with the Lactobacillus buchneri.

Treatment of corn forage with either of the Lactobacillus buchneri strains resulted in improved methane production when silage was used as a substrate in the model biogas fermentation system (FIG. 1). Strain LN4017 elicited an average improvement of 7.4% and strain LN4888 resulted in an average improvement of 1%. Although considerable differences were observed between experiments, a consistent positive response in methane production was observed in all trials.

TABLE 1

|  | Control | LN4017 | LN4888 |
|---|---|---|---|
| DM, % | 29.2 | 29.6 | 29.4 |
| Lactate, % DM | 5.92 | 3.90 | 3.89 |
| Acetate, % DM | 3.41 | 4.66 | 4.91 |
| Ethanol, % DM | 2.89 | 2.62 | 2.67 |
| Aerobic Stability, hrs | 44 | 59 | 79 |
| Fermentation Loss, % DM | 4.36 | 4.37 | 4.32 |
| Aerobic Loss, % DM | 10.75 | 8.70 | 8.49 |
| Total Ensiling Loss, % DM | 15.11 | 13.07 | 12.81 |

The economic significance of such enhancements in methane production by treatment with one of the Lactobacillus buchneri strains must consider both the amount of methane produced from each kilogram of silage and silage available for methane production. As the total recovery in the silos varies between treatments, the amount of methane produced per metric ton ensiled is enhanced with the treatments of the Lactobacillus buchneri strains. The total methane production per ton ensiled from the (1) control, (2) Lactobacillus buchneri strain LN4017 and (3) Lactobacillus buchneri strain LN4888 were 269,101 (control), 300,778 (+11.7% increase), and 279,008 (+3.7% increase), respectively.

EXAMPLE 4

Treatment of Grass Silage

The treatment of grass forage with Lactobacillus buchneri strain LN4017 produced quality silage after 60 days of fermentation when compared to the uninoculated control. TABLE 2 compares the effect of Lactobacillus buchneri strain treatment on quality of grass silage with an uninoculated control. The high content of lactic acid resulted in good preservation of the forage in all treatments as evidenced by the low fermentation DM losses as well as high amounts of acetic acid produced in relation to lactic acid.

Improved aerobic stability of the silage treated with either Lactobacillus buchneri strain LN4017 validates the acetic acid relationship with an improvement of 79 hours in stability. In addition to the increased length of time prior to heating, the effect of microbial activity is minimized as shown by the 6.6% decrease in aerobic DM losses. The total DM loss during anaerobic and aerobic fermentation was decreased by the experimental treatment by over 5% (TABLE 2).

Figure 2:
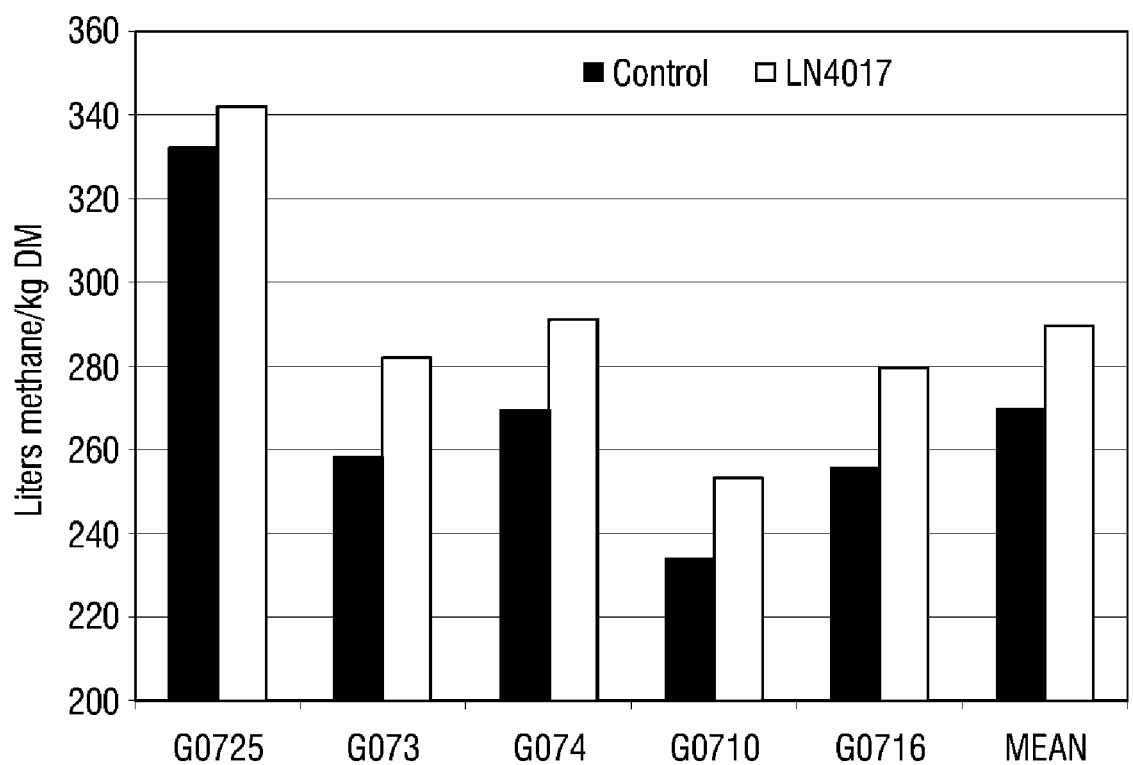
FIG. 2 shows the effect of *Lactobacillus buchneri* treatment on methane production from grass silage.

Treatment of grass forage with Lactobacillus buchneri strain LN4017 resulted in improved methane production when silage was used as a substrate in the model biogas fermentation system (FIG. 2). Strain LN4017 elicited a 7.4% improvement on average and considerable differences were observed overall with a consistently positive response in methane production. High quality silage is produced to provide a quality substrate for the production of biogas. The treated silage has a low pH and ideal ratios of lactic acid and acetic acid to provide suitable fermentation DM recovery and enhanced aerobic stability when the silage is exposed to oxygen, resulting in a higher recovery of total drug matter with enhanced nutrient composition.

TABLE 2

|  | Control | LN4017 |
|---|---|---|
| DM, % | 41.2 | 40.9 |
| Lactate, % DM | 4.51 | 2.98 |
| Acetate, % DM | 1.16 | 3.48 |
| Ethanol, % DM | 1.46 | 1.17 |

TABLE 2-continued

|  | Control | LN4017 |
|---|---|---|
| Aerobic Stability, hrs | 65 | 144 |
| Fermentation Loss, % DM | 6.27 | 7.40 |
| Aerobic Loss, % DM | 9.33 | 2.71 |
| Total Ensiling Loss, % DM | 15.60 | 10.11 |

In a systems context, similar to treatment of whole plant corn silage, the economic significance of the enhancement in methane production by treatment with *Lactobacillus buchneri* strain LN4017 prototype must include both the amount of methane produced from each kilogram of silage and the silage available for methane production. As the total recovery in the silos varies between treatments, the amount of methane produce per metric ton ensiled is enhanced with the treatment of *Lactobacillus buchneri* strain LN4017. In these trials, the total methane production per ton ensiled from the control and strain LN4017 was 227,880, and 260,681 (+14.4% increase), respectively.

EXAMPLE 5

Determination of Ferulate Esterase Activity

Lactic acid bacterial cultures, taken from Pioneer Hi-Bred International, Inc.'s microbial culture collection, were grown in De Man Rogosa Sharpe broth (MRS broth; Difco™ Lactobacilli MRS; Becton Dickinson and Company, Sparks, Md. 21152 USA), prepared as described by the manufacturer, for 24 to 48 hours. The bacterial cells were harvested from MRS broth (10 mL) by centrifugation (3200 times per gram; 20 minutes) and re-suspended in 1 mL of lysis buffer consisting of 100 mM HEPES (pH 7.0), sodium azide (10 micrograms/mL) and 5 microliters DNase (Roche Diagnostics Corporation, Indianapolis, Ind.). The cells were lysed using a French Press (French Press Cell, Pressure, SIM-AMINCO Spectronic Instruments, Inc., Rochester, N.Y.) as is known in the art. These microbial cell lysates were then assayed for ferulate esterase activity as described below.

The substrate for ferulic acid esterase activity (4-nitrophenyl ferulic acid) was purchased from the Institute of Chemistry, Slovak Academy of Sciences Dubravska, Cesta 9, 845 38, Slovakia. Ferulate esterase activities of microbial cell lysates were determined using the assay described by Mastihuba et al. (2002, Analytical Biochemistry 309: 96-101) with modifications as detailed below.

The substrate was first dissolved in dimethylsulphoxide as described by Mastihuba et al. (2002, supra) and then diluted to the final working substrate solution of 2.5 mM in 0.5M $KPO_4$; pH 7.0. Eighty microliters (80 microliters) of the substrate solution was dispensed into a 96 well microtiter plate containing twenty microliters (20 microliters) of cell lysates prepared above and the solutions were thoroughly mixed and incubated at 37 degree Celsius for 30 minutes. Control wells consisting of substrate solution in buffer (2.5 mM in 0.5M $KPO_4$; pH 7.0) and cell lysates in buffer were included and otherwise treated the same way as the reaction mixtures. Following the incubation period, 20 microliters from the reaction mixture or control wells was withdrawn using an 8-channel micropipette and added to a fresh microtiter plate well containing 180 microliters of $KPO_4$ (pH 8). The final volume in each microtiter plate well was 200 microliters. The solutions were mixed thoroughly and their optical densities determined at 405 nm using a microtiter plate reader (Vmax Kinetic Microplate Reader, Molecular Devices, Menlo Park, Calif.).

Reaction mixture absorbance readings were corrected for absorbance readings of controls prepared as described above. P-nitrophenol (0, 0.025, 0.05, 0.1, 0.15, 0.2 and 0.25 mM in 0.5 M $KPO_4$ (pH 8); 200 microliters (Sigma Chemical Company, St Louis, Mo.; Cat #104-8) was used as a standard for the ferulate esterase assay. Protein concentrations of the cells were determined using Bradford reagent as is known in the art (Sigma Chemical Company, St Louis Mo.; Cat #B 6916; Bradford, (1976) Analytical Biochemistry 72: 248-254). Ferulate esterase activities of the cell lysates were expressed as nanomoles of P-nitrophenyl (pNP) released per minute per mg of protein. Ferulate esterase activities of lactic acid bacteria ranged from 1.69 to 23.0 nanomoles p-nitrophenol released per mg protein per minute.

Having illustrated and described the principles of the embodiments of the present invention, it should be apparent to persons skilled in the art that the embodiments of the invention can be modified in arrangement and detail without departing from such principles. We claim all modifications that are within the spirit and scope of the appended claims.

All publications and published patent documents cited in this specification are incorporated herein by reference to the same extent as if each individual publication or published patent document was specifically and individually indicated to be incorporated by reference.

What is claimed is:

1. A method for enhancing biogas production from plant silage, said method comprising:
    adding an effective amount of a ferulate esterase containing composition to said silage, wherein said ferulate esterase is derived from a biologically pure culture of a ferulate esterase producing *Lactobacillus buchneri* strain, wherein said *Lactobacillus buchneri* strain is selected from the group consisting of *Lactobacillus buchneri*, strain LN4017, deposited as Patent Deposit No. PTA-6138; *Lactobacillus buchneri*, strain LN4888, deposited as Patent Deposit NRRL B-30866; and mixtures thereof;
    adding said silage to a biogas generator; and
    producing an increased amount of biogas in comparison to silage not treated with a ferulate esterase containing composition.

2. The method of claim 1, wherein the ferulate esterase containing composition added to the silage is an effective catalytic amount of the ferulate esterase producing *Lactobacillus buchneri* strain to treat the silage.

3. The method of claim 1, wherein the *Lactobacillus buchneri* contains from about $10^1$ to about $10^{10}$ viable organisms of said *Lactobacillus buchneri* per gram of said silage.

4. The method of claim 1, wherein the *Lactobacillus buchneri* contains from about $10^2$ to about $10^7$ viable organisms of said *Lactobacillus buchneri* per gram of said silage.

5. The method of claim 1, wherein the *Lactobacillus buchneri* contains from about $10^3$ to about $10^6$ viable organisms of said *Lactobacillus buchneri* per gram of said silage.

6. The method of claim 1 further comprising preventing aerobic deterioration of said plant silage.

7. The method of claim 1, wherein the plant silage is selected from the group consisting of grasses, maize, alfalfa, wheat, legumes, sorghum, sunflower, barley and mixtures thereof.

8. The method of claim 1, wherein the biogas produced is methane.

* * * * *